(12) United States Patent
Van Schie et al.

(10) Patent No.: US 10,597,675 B2
(45) Date of Patent: Mar. 24, 2020

(54) DOWNY MILDEW RESISTANCE PROVIDING GENES IN SUNFLOWER

(71) Applicant: SCIENZA BIOTECHNOLOGIES 5 B.V., Enkhuizen (NL)

(72) Inventors: Christianus Cornelis Nicolaas Van Schie, Amsterdam (NL); Tieme Zeilmaker, Amersfoort (NL)

(73) Assignee: SCIENZA BIOTECHNOLOGIES 5 B.V., Enkhuizen (NL)

( * ) Notice: Subject to any disclaimer, the term of this patent is extended or adjusted under 35 U.S.C. 154(b) by 28 days.

(21) Appl. No.: 15/990,182

(22) Filed: May 25, 2018

(65) Prior Publication Data

US 2018/0334681 A1 Nov. 22, 2018

Related U.S. Application Data

(63) Continuation of application No. 14/906,666, filed as application No. PCT/EP2014/065641 on Jul. 21, 2014, now abandoned.

(30) Foreign Application Priority Data

Jul. 22, 2013 (WO) ................. PCT/EP2013/065397

(51) Int. Cl.
C12N 15/82 (2006.01)

(52) U.S. Cl.
CPC ................................ C12N 15/8282 (2013.01)

(58) Field of Classification Search
None
See application file for complete search history.

(56) References Cited

U.S. PATENT DOCUMENTS

| | | |
|---|---|---|
| 5,866,776 A | 2/1999 | Marie De Wit |
| 6,100,451 A | 8/2000 | Chappell et al. |
| 6,271,439 B1 | 8/2001 | Johal et al. |
| 7,323,338 B2 | 1/2008 | Amir |
| 7,777,097 B2 | 8/2010 | Glazebrook et al. |
| 8,237,019 B2 | 8/2012 | Van Den Ackerveken et al. |
| 8,354,570 B2 | 1/2013 | Van Den Ackerveken et al. |
| 8,569,064 B2 | 10/2013 | Spangenberg et al. |
| 8,575,432 B2 | 11/2013 | Van Den Ackerveken et al. |
| 8,742,207 B2 * | 6/2014 | Van Damme ........ C12N 9/0071 800/305 |
| 8,796,511 B2 | 8/2014 | Van Den Ackerveken et al. |
| 9,121,029 B2 | 9/2015 | Van Damme et al. |
| 9,546,373 B2 | 1/2017 | Van Damme et al. |
| 9,932,600 B2 | 4/2018 | Van Damme et al. |
| 9,994,861 B2 | 6/2018 | Van Damme et al. |
| 2003/0172396 A1 | 9/2003 | Cohen et al. |
| 2004/0031072 A1 | 2/2004 | La Rosa et al. |
| 2006/0048240 A1 | 3/2006 | Alexandrov et al. |
| 2006/0143729 A1 | 6/2006 | Alexandrov et al. |
| 2009/0210965 A1 | 8/2009 | Mccarthy |
| 2010/0115658 A1 | 5/2010 | Van Damme et al. |
| 2014/0289897 A1 | 9/2014 | Van Damme et al. |
| 2015/0052634 A1 | 2/2015 | Park et al. |
| 2016/0160233 A1 | 6/2016 | Van Schie et al. |
| 2016/0272987 A1 | 9/2016 | Gil et al. |
| 2016/0298130 A1 | 10/2016 | Van Damme et al. |
| 2016/0298131 A1 | 10/2016 | Van Damme et al. |
| 2016/0312239 A1 | 10/2016 | Gan et al. |
| 2016/0326543 A1 | 11/2016 | Van Damme et al. |
| 2016/0326544 A1 | 11/2016 | Van Damme et al. |
| 2016/0333370 A1 | 11/2016 | Van Schie et al. |
| 2017/0283826 A1 | 10/2017 | Van Schie et al. |
| 2017/0314039 A1 | 11/2017 | Van Schie et al. |
| 2018/0135071 A9 | 5/2018 | Van Damme et al. |
| 2018/0320191 A1 | 11/2018 | Van Damme et al. |
| 2018/0334681 A1 | 11/2018 | Van Schie et al. |
| 2019/0144878 A1 | 5/2019 | Van Damme et al. |
| 2019/0203223 A1 | 7/2019 | Van Schie et al. |
| 2019/0309319 A1 | 10/2019 | Van Schie et al. |
| 2019/0316143 A1 | 10/2019 | Van Damme et al. |

FOREIGN PATENT DOCUMENTS

| | | |
|---|---|---|
| EP | 0474857 A1 | 3/1992 |
| EP | 1033405 A2 | 9/2000 |
| EP | 2455473 A1 | 5/2012 |
| WO | 1996/36697 A1 | 11/1996 |
| WO | 1991/15585 A1 | 10/1997 |
| WO | 1998/004586 A2 | 2/1998 |
| WO | 1998/32325 A1 | 7/1998 |
| WO | 1999/45125 A2 | 9/1999 |
| WO | 2000/78981 A1 | 12/2000 |
| WO | 2001/055347 A1 | 8/2001 |
| WO | 2001/61021 A2 | 8/2001 |
| WO | 2002/061101 A2 | 8/2002 |
| WO | 2002/088301 A2 | 11/2002 |
| WO | 2003/000906 A2 | 1/2003 |
| WO | 2000/070016 A2 | 11/2003 |

(Continued)

OTHER PUBLICATIONS

Hill et al (Functional analysis of conserved histidines in ADP-glucose pyrophosphorylase from *Escherichia coli*. Biochem. Biophys. Res. Comm. 244:573-577, 1998) (Year: 1998).*

(Continued)

*Primary Examiner* — Medina A Ibrahim
*Assistant Examiner* — Wayne Zhong
(74) *Attorney, Agent, or Firm* — Morrison & Foerster LLP

(57) ABSTRACT

Described herein are downy mildew resistant genes in sunflower and downy mildew resistance sunflower plants. Specifically, the present invention relates to sunflower plants being resistant to the plant pathogen downy mildew, wherein the plant comprises a downy mildew resistance conferring gene encoding a protein including the amino acid sequence as shown in SEQ ID No. 2 or SEQ ID No. 4 and wherein the expression of the resistance conferring gene is reduced as compared to the expression of said resistance conferring gene in a sunflower plant not being resistant to the plant pathogen downy mildew or the enzymatic activity of said protein is reduced as compared to the enzymatic activity of said protein in a sunflower plant not being resistant to the plant pathogen downy mildew.

15 Claims, No Drawings
Specification includes a Sequence Listing.

(56) References Cited

FOREIGN PATENT DOCUMENTS

| WO | 2004/024079 A2 | 3/2004 |
|---|---|---|
| WO | 2006/032707 A2 | 3/2006 |
| WO | 2006/047358 A1 | 5/2006 |
| WO | 2007/051483 A1 | 5/2007 |
| WO | WO2007051626 A2 | 5/2007 |
| WO | 2008/092505 A1 | 8/2008 |
| WO | 2008/092659 A1 | 8/2008 |
| WO | 2013/086499 A2 | 6/2013 |
| WO | 2015/011101 A1 | 1/2015 |
| WO | 2015/029031 A1 | 3/2015 |
| WO | 2015/106796 A1 | 7/2015 |
| WO | 2015/193418 A1 | 12/2015 |
| WO | WO2019154520 A1 | 8/2019 |

OTHER PUBLICATIONS

Guo et al (Protein tolerance to random amino acid change, Proc. Natl. Acad. Sci. USA 101:9205-9210, 2004) (Year: 2004).*
Sabetta et al (sunTILL: a TILLING resource for gene function analysis in sunflower. Plant Methods 7:20, p. 1-13, 2011) (Year: 2011).*
Ardi et al., "Involvement of Epicatechin Biosynthesis in the Activation of the Mechanism of Resistance of Avocado Fruits to Colletotrichum Gloeosporioides", Physiological and Molecular Plant Pathology, vol. 53, Nov. 1998, pp. 269-285.
Aubert et al., "Transport, Compartmentation, and Metabolism of Homoserine in Higher Plant Cells", Plant Physiology, vol. 116, 1998, pp. 547-557.
Balass et al., "Identification of a Constitutive 45 kDa Soluble Protein Associated with Resistance to Downy Mildew in Muskmelon (*Cucumis melo* L.), Line PI 124111 F", Physiological and Molecular Plant Pathology, vol. 41, 1992, pp. 387-396.
Bhattacharyya et al., "Identification of a Large Cluster of Coiled Coil-Nucleotide Binding Site-Leucine Rich Repeat-Type Genes from the Rps1 Region Containing Phytophthora Resistance Genes in Soybean", Theor Appl Genet, vol. 111, 2005, pp. 75-86.
Bouchez et al., "Functional Genomics in Plants", Plant Physiology, vol. 118, 1998, pp. 725-732.
Brouwer et al., "Fine Mapping of Three Quantitative Trait Loci for Late Blight Resistance in Tomato using near Isogenic Lines (NILs) and Sub-NILs", Theoretical and Applied Genetics, vol. 108, 2004, pp. 628-638.
Brouwer et al., "QTL Analysis of Quantitative Resistance to Phytophthora Infestans (Late Blight) in Tomato and Comparisons with Potato", Genome, vol. 27, 2004, pp. 475-492.
Budiman et al., "A Deep-Coverage Tomato BAC Library and Prospects toward Development of an STC Framework for Genome Sequencing", Genome Research, vol. 10, 2000, pp. 129-136.
Burnham et al., "Quantitative Trait Loci for Partial Resistance to Phytophthora Sojae in Soybean", Crop Science, vol. 43, Sep.-Dec. 2003, pp. 1610-1617.
Charlotte, Elliott, "Relative Susceptibility to Pythium Root Rot of Twelve Dent Corn Inbreds", Journal of Agricultural Research, vol. 64, No. 12, Jun. 15, 1992, pp. 711-723.
Cho, et al., "Constitutive Expression of the Flavanone 3-Hydroxylase Gene Related to Pathotype-Specific Ascochyta Blight Resistance in *Cicer arietinum* L", vol. 67, Physiological and Molecular Plant Pathology, 2005, pp. 100-107.
Choi et al., "Predicting the Functional Effect of Amino Acid Substitutions and Indels", PLoS ONE, vol. 7, No. 10, 2012, pp. 1-13.
Clough et al., "Floral Dip: A Simplified Method for Agrobacterium-Mediated Transformation of *Arabidopsis thaliana*", The Plant Journal, vol. 16, No. 6, 1998, pp. 735-743.
Conrath et al., "Enhanced Resistance to Phytophthora Infestans and Alternaria Solani in Leaves and Tubers, Respectively, of Potato Plants with Decreased Activity of the Plastidic ATP/ADP Transporter", Planta, vol. 19, 2003, pp. 75-83.
Constantinescu et al., "Peronospora-like Fungi (*Chromista, Peronosporales*) Parasitic on Brassicaceae and Related Hosts", Nova-Hedwigia, vol. 74, May 2002, pp. 291-338.
Crowe et al., "CATMA: A Complete *Arabidopsis* GST Database", Nucleic Acids Research, vol. 31, No. 1, 2003, pp. 156-158.
Database EMBL, "*Arabidopsis thaliana* Flavanone 3-Hydroxylase-like Protein (At5g24530) mRNA, complete Cds", Retrieved from EBI Accession No. EMBL: AY081455, Apr. 15, 2002.
Database EMBL, "*Arabidopsis thaliana* Ftavanone 3-Hydroxylase-like Protein {K 18P6.6) mRNA, Complete Cds", Retrieved from EBI Accession No. EMBL: AF386975, Jun. 16, 2001.
De Wit, P. J. G. M., "Molecular Characterization of Gene-for-Gene Systems in Plant-Fungus Interactions and the Application of Avirulence Genes in Control of Plant Pathogens", Annu. Rev. Phytopathol., vol. 30, 1992, pp. 391-418.
EBI Accession No. AF082525, Available at <http://www.ebi.ac.uk/ena/data/view/AF082525&display=text>, Jun. 1, 1999, 2 pages.
EBI Database Accession No. DQ208192, Available at <http://www.ebi.ac.uk/ena/data/view/ABB20895&display=text>, Sep. 6, 2006, 2 pages.
"Federal Register", vol. 76, No. 27, Feb. 9, 2011, 14 pages.
Fischer et al., "Quantitative Trait Locus Analysis of Fungal Disease Resistance Factors on a Molecular Map of Grapevine", Theoretical and Applied Genetics, vol. 108, 2004, pp. 501-515.
Flanagan et al., "Using Sift and Polyphen to Predict Loss-of-Function and Gain-of-Function Mutations", Genet Test Mol Biomarkers, vol. 14, No. 4, 2010, pp. 533-537.
Franchel et al., "Positional cloning of a candidate gene for resistance to the sunflower downy mildew, *Plasmopara halstedii* race 300", Theoretical and Applied Genetics, vol. 126, No. 2, Feb. 2013, pp. 359-367.
Friedrich et al., "NIM1Overexpression in *Arabidopsis* Potentiates Plant Disease Resistance and Results in Enhanced Effectiveness of Fungicides", MPMI, vol. 14, No. 9, The American Phytopathological Society, 2001, pp. 1114-1124.
Gaspero et al., "Resistance Gene Analogs are Candidate Markers for Disease-Resistance Genes in Grape (*Vitis* spp.)", Theoretical and Applied Genetics, vol. 106, 2002, pp. 163-172.
"Geneseq Database Accession No. AAG45151", Oct. 18, 2000, 4 pages.
Giovanini et al., "Gene-for-Gene Defense of Wheat against the Hessian Fly Lacks a Classical Oxidative Burst", Molecular Plant-Microbe Interactions, vol. 19, No. 9, 2006, pp. 1023-1033.
Göker et al., "Phylogeny of Hyaloperonospora Based on Nuclear Ribosomal Internal Transcribed Spacer Sequences", Mycological Progres, vol. 3, No. 2, May 2004, pp. 83-94.
Göker et al., "Taxonomic aspects of Peronosporaceae inferred from Bayesian molecular phylogenetics", Canadian Journal of Botany, vol. 81, No. 7, 2003, pp. 672-683.
Gurr et al., "Engineering Plants with Increased Disease Resistance: How are we going to express it?", Trends Biotechnology, vol. 23, No. 6, Jun. 2005, pp. 283-290.
Gurr et al., "Engineering Plants with Increased Disease Resistance: What are we going to express?", Trends Biotechnology, vol. 23, No. 6, Jun. 2005, pp. 275-282.
Guzzo Thesis, "Isolation of cv. Mundo Novo Coffee Plant Genes Associated with Systemic Acquired Resistance", Jun. 2004, 21 pages.
Hellens et al., "pGreen: A Versatile and Flexible Binary Ti Vector for Agrobacterium-Mediated Plant Transformation", Plant Molecular Biology, vol. 42, 2000, pp. 819-832.
Henikoff et al., "TILLING. Traditional Mutagenesis Meets Functional Genomics", Plant Physiology, vol. 135, 2004, pp. 630-636.
Holub et al., "Phenotypic and Genotypic Characterization of Interactions between Isolates of Peronospora Parasitica and Accessions of *Arabidopsis thaliana*", vol. 7, No. 2, 1994, pp. 223-239.
Hong et al., "First confirmed report of downy mildew caused by Hyaloperonospora parasitica on broccoli in Korea", Plant Pathology, vol. 57, No. 4, Aug. 2008, p. 777.
Jong et al., "Membrane-Associated Transcripts in *Arabidopsis*; Their Isolation and Characterization by DNA Microarray Analysis and Bioinformatics", The Plant Journal, vol. 46, 2006, pp. 708-721.

(56) References Cited

OTHER PUBLICATIONS

Karimi et al., "GATEWAY Vectors for Agrobacterium-Mediated Plant Transformation", Trends in Plant Science, vol. 7, No. 5, May 2002, pp. 193-195.
Kim et al., "Characterization of Late Blight Resistance Derived from Solanum Pimpinellifolium L3708 against Multiple Isolates of the Pathogen Phytophthora Infestans", Journal of the American Society for Horticultural Science, vol. 131 No. 5, 2006, pp. 637-645.
Kitz, Leilani, "Evaluation of Downy Mildew (*Peronospora farinosa* f.sp. *chenopodii*) Resistance among Quinoa Genotypes and Investigation of *P. farinosa* Growth using Scanning Electron Microscopy", All Theses and Dissertations, Brigham Young University, 2008, 134 pages.
Kofoet et al., "Inheritance of Resistance to Downy Mildew (*Peronospora destructor* [Berk.] Casp.) from *Allium roylei* Steam in the Backcross *Allium cepa* L. × (*A. roylei* ×*A. cepa*)", Plant Breeding, vol. 105, 1990, pp. 144-149.
Kortekamp, A., "Expression Analysis of Defence-Related Genes in Grapevine Leaves after Inoculation with a Host and a Non-Host Pathogen", Plant Physiology and Biochemistry, vol. 44, 2006, pp. 58-67.
Ku et al., "Comparing Sequenced Segments of the Tomato and *Arabidopsis* Genomes: Large-Scale Duplication Followed by Selective Gene Loss Creates a Network of Synteny", PNAS, vol. 97, No. 16, Aug. 1, 2000, pp. 9121-9126.
Lacomme et al., "Bax-Induced Cell Death in Tobacco is Similar to the Hypersensitive Response", Cell Biology, Proc. Natl. Acad. Sci. U.S.A., vol. 96, No. 14, Jul. 1999, pp. 7956-7961.
Lamour et al., "Oomycete Genetics and Genomics: Diversity, Interactions and Research Tools", Wiley-Blackwell, 2009, 6 pages.
Lebeda, A.,"Screening of Wild *Cucumis* Species against Downy Mildew (*Pseudoperonospora cubensis*) Isolates from Cucumbers", Phytoparasitica, vol. 20, No. 3, 1992, pp. 203-210.
Lee et al., "Identification of the Gene Encoding Homoserine Kinase from *Arabidopsis thaliana* and Characterization of the Recombinant Enzyme Derived from the Gene", Archives Biochemistry Biophysics, vol. 372, No. 1, Dec. 1999, pp. 135-142.
Lee et al., "Methionine and Threonine Synthesis are Limited by Homoserine Availability and not the Activity of Omoserine Kinase in *Arabidopsis thaliana*", The Plant Journal, vol. 41, 2005, pp. 685-696.
Mae et al., "Transgenic Plants Producing the Bacterial Pheromone N-Acyl-Homoserine Lactone Exhibit Enhanced Resistance to the Bacterial Phytopathogen *Erwinia carotovora*", Molecular Plant-Microbe Interactions, vol. 14, No. 9, 2001, pp. 1035-1042.
Mccallum et al., "Targeted Screening for Induced Mutations", Nature Biotechnology, vol. 18, Apr. 2000, pp. 455-457.
Meer et al., "An Interspecific Cross between *Allium roylei* Steam and *Allium cepa* L., and its Backcross to *A. cepa*", Euphytica, vol. 47, 1990, pp. 29-31.
Mercedes, Dana et al., "Transgenic Tobacco Plants Overexpressing Chitinases of Fungal Origin Show Enhanced Resistance to Biotic and Abiotic Stress Agents", Plant Physiology, vol. 142, Oct. 2006, pp. 722-730.
Mosher et al., "A Comprehensive Structure-Function Analysis of *Arabidopsis* SNI1 Defines Essential Regions and Transcriptional Repressor Activity", vol. 18, The Plant Cell, Jul. 2006, pp. 1750-1765.
Parker et al., "Characterization of eds1, a Mutation in *Arabidopsis* Suppressing Resistance to Peronospora Parasitica Specified by Several Different RPP Genes", Plant Cell, vol. 8, Nov. 1996, pp. 2033-2046.
Perchepied et al., "Relationship Between Loci Conferring Downy Mildew and Powdery Mildew Resistance in Melon Assessed by Quantitative Trait Loci Mapping", Phytopathology, vol. 95, No. 5, 2005, pp. 556-565.

Radwan et al., "Molecular Characterization of Two Types of Resistance in Sunflower to Plasmopara halstedii, the Causal Agent of Downy Mildew", The American Phytopathological Society, vol. 101, No. 8, 2011, pp. 971-979.
Rostas et al., "Copper and Herbivory Lead to Priming and Synergism in Phytohormones and Plant Volatiles in the Absence of Salicylate-Jasmonate Antagonism", Plant Signaling & Behavior, vol. 8, No. 6, Jun. 2013, pp. e24264-1-e24264-3.
Russell, G. E., "Some Effects of Inoculation With Yellowing Viruses on the Susceptibility of Sugar Beet to Fungal Pathogens: I. Susceptibility to Peronospora Farinosa", Transactions of the British Mycological Society, vol. 49, No. 4, 1966, pp. 611-619.
Sabetta et al., "sunTILL: a TILLING resource for gene function analysis in sunflower", Plant Methods 2011, vol. 7, No. 20, 2011, pp. 1-13.
Sandhu et al., "Soybean Phytophthora Resistance Gene Rps8 Maps Closely to the Rps3 Region", Journal of Heredity, vol. 96, No. 5, Jun. 15, 2005, pp. 536-541.
Sim et al., "SIFT web server: predicting effects of amino acid substitutions on proteins", Nucleic Acids Res., vol. 40, Web Server issue, 2012, 6 pages.
Sinapidou et al., "Two TIR:NB:LRR Genes are Required to Specify Resistance to Peronospora Parasitica Isolate Cala2 in *Arabidopsis*", The Plant Journal, vol. 38, 2004, pp. 898-909.
Skadhauge, et al., "The Role of the Barley Testa Layer and Its Flavonoid Content in Resistance to Fusarium Infections", vol. 126, Carlsberg Laboratory, Department of Physiology, 1997, pp. 147-160.
Sun, et al., "Silencing of Six Susceptibility Genes Results in Potato Late Blight Resistance", Transgenic Research, vol. 25, 2016, pp. 731-742 (with 12 pages of Supplementary Copy).
Szwacka et al., "Variable Properties of Transgenic Cucumber Plants Containing the Thaumatin II Gene from Thaumatococcus Daniellii", Acta Physiologiae Plantarum, vol. 24. No. 2, 2002, pp. 173-185.
Takatsuji, Hiroshi, "Development of Disease-Resistant Rice Using Regulatory Components of Induced Disease Resistance", Frontiers in Plant Science, vol. 5, Article 630, Nov. 13, 2014, 12 pages.
Thomas et al., "Linkage of Random Amplified Polymorphic DNA Markers to Downy Mildew Resistance in Cucumber (*Cucumis sativus* L.)", Euphytica, vol. 115, No. 2, 2000, pp. 105-113.
Thomazella et al., "CRISPR-Cas9 Mediated Mutagenesis of a DMR6 Ortholog in Tomato Confers Broad-Spectrum Disease Resistance", Department of Plant and Microbial Biology, University of California, Berkeley, Berkeley CA 94720, Jul. 2016, pp. 1-23.
Till et al., "Mismatch cleavage by single-strand specific nucleases", Nucleic Acids Research, vol. 32, No. 8, 2004, pp. 2632-2641.
Tor et al., "*Arabidopsis* Downy Mildew Resistance Gene RPP27 Encodes a Receptor-Like Protein Similar to CLAVATA2 and Tomato Cf-9 1", vol. 135, Plant Physiology, Jun. 2004, pp. 1100-1112.
Uniprot Database Accession No. K4C928, Available at <http://www.uniprot.org/uniprot/K4C928.txt> Nov. 28, 2012, pages.
Uniprot Database Accession No. M0ZIQ1, Available at <http://www.uniprot.org/uniprot/M0ZIQ1.txt>, Apr. 3, 2013, 2 pages.
Uniprot Database Accession No. M1CK41, Available at < Database Accession No. M1CK41> Apr. 3, 2013, 2 pages.
Vailleau et al., "A R2R3-MYB Gene, AtMYB30, Acts as a Positive Regulator of the Hypersensitive Cell Death Program in Plants in Response to Pathogen Attack", vol. 99, No. 15, Jul. 23, 2002, pp. 10179-10184.
Van Damme et al., "*Arabidopsis* DMR6 encodes a putative 2OG-Fe(II) oxygenase that is defense-associated but equired for susceptibility to downy mildew", The Plant Journal, vol. 54, Jun. 2008, pp. 785-793.
Van Damme et al., "Downy Mildew Resistance in *Arabidopsis* by Mutation of Homoserine Kinase", The Plant Cell, vol. 21, Jul. 2009, pp. 2179-2189.
Van Damme et al., "Identification of *Arabidopsis loci* Required for Susceptibility to the Downy Mildew Pathogen *Hyaloperonospora parasitica*", Molecular Plant-Microbe Interactions, vol. 18, No. 6, 2005, pp. 583-592.
Van Damme, Mirelle, "Genetic Analysis of Disease Susceptibility in the *Arabidopsis-Hyaloperonospora parasitica* Interaction", Thesis, 2007, 134 pages.

(56) References Cited

OTHER PUBLICATIONS

Vandenbussche et al., "Generation of a 3D Indexed Petunia Insertion Database for Reverse Genetics", The Plant Journal, vol. 54, 2008, pp. 1105-1114.
Voglmayr, Hermann, "Phylogenetic Relationships of Peronospora and Related Genera Based on Nuclear Ribosomal Its Sequences", Mycol Res., vol. 107, No. 10, 2003, pp. 1132-1142.
Weaver et al., "The *Arabidopsis thaliana* Tir-Nb-Lrr R-Protein, Rpp1a; Protein Localization and Constitutive Activation of Defence by Truncated Alleles in Tobacco and *Arabidopsis*", vol. 47, The Plant Journal, 2006, pp. 829-840.
Xu et al., "Genome Sequence and Analysis of the Tuber Crop Potato", Nature, vol. 475, Jul. 14, 2011, pp. 189-195.
Yang et al., "Characterization and Mapping of Rpi1, A Gene that Confers Dominant Resistance to Stalk Rot in Maize", Molecular Genetics and Genomics, vol. 274, 2005, pp. 229-234.
Zeilmaker et al., "Downy Mildew Resistant 6 and DMR6-Like Oxygenase 1 are Partially Redundant but Distinct Suppressors of Immunity in *Arabidopsis*", The Pant Journal, vol. 81, 2015, pp. 210-222.
Zeilmaker, Tieme, "Functional and Applied Aspects of the Downy Mildew Resistant 1 and 6 Genes in *Arabidopsis*", Universiteit Utrecht, Available at <http://web.science.uu.nl/pmi/publications/PDF/2012/Proefschrift-Zeilmaker-2012.pdf>, Feb. 6, 2012, 147 pages.
Zhang et al., "Salicylic Acid 3-Hydroxylase Regulates *Arabidopsis* Leaf Longevity by Mediating Salicylic Acid Catabolism", Proceedings of the National Academy of Sciences of the United States of America, vol. 110, No. 36, Sep. 3, 2013, pp. 14807-14812.
Zhang, James Z., "Overexpression Analysis of Plant Transcription Factors", Curr Opin Plant Biol., vol. 6, No. 5, 2003, pp. 430-440.
Zimmermann et al., "Gene-Expression Analysis and Network Discovery using Genevestigator", Trends Plant Sci., vol. 10, No. 9, Sep. 2005, pp. 407-409.
Alignment of primers with the two copies of the cabbage DMR6 Gene, filed in Opposition against EP2455477, dated Sep. 7, 2016, 4 pages.
Amended claims filed after receipt of (European) search report, filed Jul. 30, 2009, during prosecution of EP2115147, 5 pages.
Amended claims filed after receipt of (European) search report, filed Nov. 19, 2012, during prosecution of EP2455479, 2 pages.
Amended claims filed after receipt of (European) search report, filed Jan. 22, 2013, during prosecution of EP2455482, 2 pages.
Amended claims filed after receipt of (European) search report, filed Jan. 22, 2013, during prosecution of EP2455483, 2 pages.
Amended claims filed after receipt of (European) search report, filed Sep. 5, 2016, during prosecution of EP3024929, 2 pages.
Amended claims filed after receipt of (European) search report, filed Feb. 10, 2017, during prosecution of EP3094722, 1 page.
Amended claims submitted by applicant dated Sep. 25, 2017 for EP2681234 examination proceedings, filed Dec. 7, 2017 in Opposition against EP2455477, 1 page.
Amended claims with annotations, filed Sep. 10, 2018, during appeal of EP2455473, 14 pages.
Amended claims with annotations, filed Apr. 26, 2018, during appeal of EP2455473, 2 pages.
Amended claims, filed Feb. 2, 2012, during prosecution of EP2115147, 2 pages.
Amended claims, filed Aug. 20, 2010, during prosecution of EP2115147, 4 pages.
Amended claims, filed May 26, 2011, during prosecution of EP2115147, 3 pages.
Amended claims, filed Mar. 17, 2017, during prosecution of EP2455474, 1 page.
Amended claims, filed Oct. 15, 2018, during prosecution of EP3024929, 1 page.
Amended claims, filed Dec. 21, 2017, during prosecution of EP3024929, 2 pages.
Amended claims, filed Jan. 17, 2018, during prosecution of EP3094722, 1 page.
Amended claims, filed May 28, 2018, during prosecution of EP3094722, 1 page.
Amended claims, filed Apr. 17, 2018, during prosecution of EP3167051, 1 page.
Amended claims, filed Aug. 17, 2017, during prosecution of EP3167051, 2 pages.
Amended claims, filed May 28, 2018, during prosecution of EP3167051, 1 page.
Amended description with annotations, filed Jun. 5, 2012, during prosecution of EP2115147, 7 pages.
Amended description with annotations, filed Oct. 21, 2013, during prosecution of EP2455473, 11 pages.
Amended description with annotations, filed Oct. 10, 2016, during prosecution of EP2455474, 29 pages.
Amended description with annotations, filed Mar. 17, 2017, during prosecution of EP2455474, 29 pages.
Amended description with annotations, filed Aug. 30, 2016, during prosecution of EP2455475, 30 pages.
Amended description with annotations, filed Jul. 21, 2016, during prosecution of EP2455476, 29 pages.
Amended description with annotations, filed Oct. 21, 2013, during prosecution of EP2455477, 11 pages.
Amended description with annotations, filed Oct. 10, 2016, during prosecution of EP2455478, 29 pages.
Amended description with annotations, filed Oct. 5, 2016, during prosecution of EP2455479, 30 pages.
Amended description with annotations, filed Jul. 21, 2016, during prosecution of EP2455480, 29 pages.
Amended description with annotations, filed Aug. 30, 2016, during prosecution of EP2455481, 29 pages.
Amended description with annotations, filed Jan. 17, 2018, during prosecution of EP3094722, 19 pages.
Amended description with annotations, filed May 28, 2018, during prosecution of EP3094722, 19 pages.
Amended description with annotations, filed Apr. 17, 2018, during prosecution of EP3167051, 17 pages.
Amended description with annotations, filed May 28, 2018, during prosecution of EP3167051, 34 pages.
Amendments received before examination, filed Nov. 19, 2012, during prosecution of EP2455479, 3 pages.
Amendments received before examination, filed Jan. 22, 2013, during prosecution of EP2455482, 3 pages.
Amendments received before examination, filed Jan. 22, 2013, during prosecution of EP2455483, 3 pages.
Amendments received before examination, filed Sep. 5, 2016, during prosecution of EP3024929, 2 pages.
Amendments received before examination, filed Feb. 10, 2017, during prosecution of EP3094722, 2 pages.
Amendments received before examination, filed Aug. 17, 2017, during prosecution of EP3167051, 3 pages.
Analysis performed by Dr. Tieme Zeilmaker using the protein analysis program Provean, filed Sep. 15, 2017, in Opposition against EP2455473, 3 pages.
Annex B, filed by the Applicant on Aug. 30, 2016, in the case EP2455475 during the examination, 6 pages.
Annexes (other than cited documents) regarding appeal procedure, Sep. 10, 2018, filed during appeal of EP2455473, 6 pages.
Applicant request for correction/amendment of the text proposed for grant and amended claims, filed Jan. 15, 2019 in case EP3167051, 3 pages.
Applicant request for correction/amendment of the text proposed for grant, filed Aug. 17, 2017 in case EP2455475, 1 page.
Argentina Application No. P180102445, filed on Aug. 29, 2018, (Copy Not Attached).
Auxiliary request containing amended claims, filed Sep. 15, 2017, in Opposition against EP2455473, 1 page.
Auxiliary request containing amended claims, filed Dec. 19, 2017, in Opposition against EP2455473, 1 page.
Auxiliary Request I, filed Apr. 26, 2018, during appeal of EP2455473, 1 page.
Belhaj et al. (2013). "Plant genome editing made easy: targeted mutagenesis in model and crop plants using the CRISPR/Cas system," Plant Methods, 9(39): 1-10.

(56) References Cited

OTHER PUBLICATIONS

Blast comparison between the amino acid sequences of *Arabidopsis* DMR6 (query ID Query_190785) and XP 013593012.1, dated Sep. 21, 2017, 2 pages.
Blast comparison between the amino acid sequences of *Arabidopsis* DMR6 (query ID Query_236939) and XP 013620820.1, dated Sep. 21, 2017, 2 pages.
Blast comparison results of query ID 258413, filed during prosecution of EP2455475, dated Aug. 30, 2016, 6 pages.
Blast comparison results of query ID 3871 and subject ID 3873, filed during prosecution of EP2455474, dated Jul. 3, 2013, 2 pages.
Blast comparison results of query ID XP_003526765.1 and subject ID OAO94377.1, filed during prosecution of EP2455481, dated Aug. 30, 2016, 2 pages.
Blast strategy and results on Solanum lycopersicum nucleotide sequence, filed Jul. 18, 2018, in Opposition against EP2455479, 2 pages.
Blast strategy and results on Solanum lycopersicum protein sequence, filed Jul. 18, 2018, in Opposition against EP2455479, 5 pages.
Blast-P query of AtF3H against *A.thaliana* genome, filed in Opposition against EP2455477, dated Dec. 7, 2017, 3 pages.
Brandenberger et al., (1992). "Evaluation of 1-7 Spinach Germplasm for Resistance to a New Race (Race 4) of *Peronospora farinosa* f. sp. *spinaciae*," Hortscience, 27(20):1118-1119.
Brandenberger et al., (1994). "Characterization of resistance of spinach to white rust (*Albugo occidentalis*) and downy mildew (*Peronospora farinosa* f. sp. *spinaciae*)," Phytopathology, 84(4):431-437.
Chen et al., (2008). "Host specificity and tomatorelated race composition of Phytophthora infestans isolates in Taiwan during 2004 and 2005," Plant Disease, 92(5):751-755.
Coelho et al., (2003). "Expression of resistance to downy mildew at cotyledon and adult plant stages in *Brassica oleracea* L.," Euphytica, 133(3):279-284.
Communication from the Examining Division for EP2455473 dated Mar. 20, 2014, filed in Appeal proceedings for EP2455473, 1 page.
Communication from the Examining Division for EP2455477 dated Nov. 14, 2013, filed in Opposition against EP2455477, 2 pages.
Communication from the Examining Division for EP2681234 dated Nov. 20, 2017, filed in Opposition against EP245577, 4 pages.
Communication from the Examining Division in case EP2455475 dated Mar. 20, 2014, concerning the staying of examination proceedings, 1 page.
Communication from the Examining Division dated Mar. 20, 2014, filed in Opposition against EP2455474, 1 page.
Communication from the Examining Division dated Mar. 20, 2014, filed in Opposition against EP2455479, 1 page.
Communication pursuant to Art. 94(3) EPC dated Mar. 8, 2017, filed Dec. 14, 2018 in Opposition against EP2455474, 3 pages.
Cooke et al., (2000). "A molecular phylogeny of Phytophthora and related Oomycetes," Fungal Genetics and Biology, 30:17-32.
Curriculum vitae of Dr. Tieme Zeilmaker, filed Sep. 15, 2017, in Opposition against EP2455473, 2 pages.
CV of Dr. Adriaan Verhage, dated Oct. 20, 2017, submitted in opposition proceedings for EP2455473, 3 pages.
Data on sequence and resistance of spinach variants, filed Feb. 14, 2017, in Opposition against EP2455473, 3 pages.
Declaration and CV of Dr. A. Rijpkema, dated Jul. 27, 2018, submitted in opposition proceedings for EP2455474, 4 pages.
Declaration and CV of Dr. B. D'hoop, dated Jul. 27, 2018, submitted in opposition proceedings for EP2455474, 3 pages.
Declaration and CV of Dr. P.M. Eggink, dated Jul. 14, 2018, submitted in opposition proceedings for EP2455479, 3 pages.
Declaration by Dr. A. Verhage, dated Jun. 26, 2017, submitted in opposition proceedings for EP2455474 and EP2455479, 1 page.
Declaration of Dr. Adriaan Verhage, dated Oct. 17, 2017, submitted in opposition proceedings for EP2455473, 2 pages.
Develey-Riviere et al., (2007). "Resistance to pathogens and host developmental stage: a multifaceted relationship within the plant kingdom," New Phytologist, 175:405-416.
Disease test results DMR6 Spinach mutants, filed Jul. 17, 2017, in Opposition against EP2455473, 1 page.
Enza lettuce catalogue, dated Jan. 17, 2014, filed in Opposition to EP2115147, p. 102-115.
Experimental data "Annex A—Overview supporting data DMR6 down regulation and disease resistance" filed Jul. 18, 2018, in Opposition against EP2455479, 6 pages.
Experimental data "Annex A—Overview supporting data DMR6 down regulation and disease resistance," filed Oct. 10, 2016 by the Applicant, during the examination of EP2455474, 28 pages.
Experimental data on mutation in dmr6 conferring resistance to cabbage, filed during Opposition against EP2455477, dated Jan. 18, 2018, 3 pages.
Experimental data showing no Phytophthora resistance, filed during prosecution of EP3167051, dated Aug. 17, 2017, 1 page.
Experimental data showing that the claimed sunflower plants are resistant to downy mildew, filed during prosecution of EP3024929, dated Dec. 21, 2017, 2 pages.
Fall et al., (2015). "Infection Efficiency of Four Phytophthora infestans Clonal Lineages and DNA-based Quantification of Sporangia," PLoS ONE, 10(8): e0136312doi: 10.1371/journal.pone.0136312, 18 pages.
Further experimental data of pathogen resistance against Phytophthora infestans of mutated tomato plants, filed during Opposition against EP2455479, dated Jan. 4, 2019, 2 pages.
Grimplet, et al., (2007). "Tissue-Specific mRNA Expression Profiling in Grape Berry Tissues", BMC Genomics, vol. 8, No. 187, pp. 1-23.
Instructions to the PhD candidate, filed Jul. 17, 2017, in Opposition against EP2455473, Utrecht University, 11 pages.
International Seed Federation Guidelines for Coding Pests of Vegetable and Cereal Crops, submitted in Opposition against EP2455477, dated Jan. 18, 2018, 4 pages.
Irish et al., (2007). "Three new races of the spinach downy mildew pathogen identified by a modified set of spinach differentials," Plant Disease, 91(11):1392-1396.
Kofoet et al., (1990). "Resistance to Downy Mildew (*Peronospora destructor* (Berk.) Casp.) in *Allium* Species//Resistenz Gegen Falschen Mehltau (*Peronospora destructor* (Berk.) Casp.) in *Allium*-Arten," Zeitschrift Fuer Pflanzenkrankheiten Uno Pflanzenschutz//Journal of Plant Diseases and Protection, 97(1):13-23.
Letter accompanying subsequently filed items, filed during prosecution of EP2455473, dated Mar. 10, 2014, 1 page.
Letter accompanying subsequently filed items, filed during prosecution of EP2455474, dated Mar. 10, 2014, 1 page.
Letter accompanying subsequently filed items, filed during prosecution of EP2455475, dated Mar. 10, 2014, 1 page.
Letter accompanying subsequently filed items, filed during prosecution of EP2455476, dated Mar. 10, 2014, 1 page.
Letter accompanying subsequently filed items, filed during prosecution of EP2455477, dated Mar. 10, 2014, 1 page.
Letter accompanying subsequently filed items, filed during prosecution of EP2455481, dated Mar. 10, 2014, 1 page.
Letter accompanying subsequently filed items, filed during prosecution of EP2455482, dated Mar. 10, 2014, 1 page.
Letter regarding the opposition procedure (no time limit) and Auxiliary requests I and II, filed during Opposition against EP2455477, dated Dec. 8, 2017, 22 pages.
Letter regarding the opposition procedure (no time limit), filed during Opposition against EP2455473, dated Sep. 14, 2017, 3 pages.
Letter regarding the opposition procedure (no time limit), filed during Opposition against EP2455473, dated Sep. 15, 2017, 17 pages.
Letter regarding the opposition procedure (no time limit), filed during Opposition against EP2455477, dated Jan. 18, 2018, 15 pages.
Letter regarding the opposition procedure and Auxiliary requests I and II, filed during Opposition against EP2455474, dated Dec. 14, 2018, 39 pages.
Letter regarding the opposition procedure and Auxiliary requests I and II, filed during Opposition against EP2455479, dated Jan. 8, 2019, 48 pages.

(56) References Cited

OTHER PUBLICATIONS

Lukacin et al., (1997). "Identification of strictly conserved histidine and arginine residues as part of the active site in Petunia hybrida flavanone 3P-hydroxylase," Eur. J. Biochem., 249:748-757.
Multiple alignment of cabbage DMR6 (*B.oleracea*) with known oxidoreductases, filed May 22, 2017, in Opposition against EP2455477, 2 pages.
Multiple alignment of spinach DMR6 (*S.oleracea*) with known oxidoreductases, filed Feb. 14, 2017, in Opposition against EP2455473, 1 page.
NCBI Reference Sequence NP_190692.1, dated Jul. 3, 2013, filed in Opposition against EP2455473 and during prosecution for EP2455474 and EP2455479, 2 pages.
NCBI Reference Sequence NP_197841.1, dated Nov. 25, 2016, filed in Opposition against EP2455473 and during prosecution for EP2455474 and EP2455479, 2 pages.
Non-Final Office Action received for U.S. Appl. No. 15/111,285, dated Feb. 7, 2018, 13 pages.
Notice of appeal by Bird&Bird, filed in relation to EP2455473, dated Feb. 22, 2018, 2 pages.
Notice of appeal by Bird&Bird, filed in relation to EP2455477, dated Jul. 19, 2018, 2 pages.
Nowicki et al., (2012). "Potato and Tomato late blight caused by Phytophthora infestans: An overview of pathology and resistance breeding," Plant Disease, 96(1):4-17.
Official variety description spinach variety *bandola* by the Naktuinbouw (1995), filed in Opposition against EP2455473, 1 page.
Official variety description spinach variety *maracas* by the Naktuinbouw (1950), filed in Opposition against EP2455473, 1 page.
Official variety description spinach variety *marimba* by the Naktuinbouw (1950), filed in Opposition against EP2455473, 1 page.
Official variety description spinach variety *symphony* by the Naktuinbouw (1950), filed in Opposition against EP2455473, 3 pages.
Pacific Pests and Pathogens Fact Sheet on cabbage downy mildew, dated Sep. 20, 2017, 3 pages.
Partial set of drawings filed in response to formal objections, filed during prosecution of EP2455474, dated Mar. 13, 2012, 4 pages.
Partial set of drawings filed in response to formal objections, filed during prosecution of EP2455475, dated Mar. 13, 2012, 4 pages.
Partial set of drawings filed in response to formal objections, filed during prosecution of EP2455476, dated Mar. 13, 2012, 4 pages.
Partial set of drawings filed in response to formal objections, filed during prosecution of EP2455477, dated Mar. 13, 2012, 4 pages.
Partial set of drawings filed in response to formal objections, filed during prosecution of EP2455478, dated Mar. 13, 2012, 4 pages.
Partial set of drawings filed in response to formal objections, filed during prosecution of EP2455479, dated Mar. 13, 2012, 4 pages.
Partial set of drawings filed in response to formal objections, filed during prosecution of EP2455480, dated Mar. 13, 2012, 4 pages.
Partial set of drawings filed in response to formal objections, filed during prosecution of EP2455481, dated Mar. 13, 2012, 4 pages.
Partial set of drawings filed in response to formal objections, filed during prosecution of EP2455482, dated Mar. 13, 2012, 4 pages.
Partial set of drawings filed in response to formal objections, filed during prosecution of EP2455483, dated Mar. 13, 2012, 4 pages.
PCT Application No. PCT/EP2018/073019, filed on Aug. 27, 2018, (Copy Not Attached).
Pihlajamaa, Presentation slides taken from conference documentation, Presentation at the 8th conference on Intellectual Property Protection for Plant Innovation 2017, p. 197-205.
Preliminary Amendment, filed for U.S. Appl. No. 15/594,293, dated May 12, 2017, 7 pages.
Preliminary Amendment, filed for U.S. Appl. No. 15/975,670, dated Jul. 23, 2018, 5 pages.
Preliminary Amendment, filed for U.S. Appl. No. 15/990,182, dated Aug. 13, 2018, 5 pages.
Preliminary Amendment, filed for U.S. Appl. No. 16/055,697, dated Aug. 6, 2018, 9 pages.
Primrose et al., (2006). "Principles of Gene Manipulation and Genomics," Chapter 9 of Bioinformatics, Blackwell Publishing, 21 pages.
Protocol for Distinctness, Uniformity and Stability Tests for *Spinach oleracea* L. (2002). European Union Community Plant Variety Office, Final CPVO-TP-55-6 Final, 17 pages.
Qin et al., "Whole-Genome Sequencing of Cultivated and Wild Peppers Provides Insights into Capsicum Domestication and Specialization", PNAS, vol. 111, No. 14, Apr. 8, 2014, pp, 5135-5140.
Reply of the patent proprietor to the notice(s) of opposition dated Jul. 11, 2014, filed during Opposition against EP2115147, 5 pages.
Reply of the patent proprietor to the notice(s) of opposition dated Feb. 13, 2017, filed during Opposition against EP2455473, 28 pages.
Reply of the patent proprietor to the notice(s) of opposition dated May 22, 2017, filed during Opposition against EP2455477, 30 pages.
Reply to appeal by Bird&Bird filed in relation to EP2455473, dated Sep. 10, 2018, 40 pages.
Reply to communication from the Examining Division, filed during prosecution of EP2115147, dated Feb. 2, 2012, 3 pages.
Reply to communication from the Examining Division, filed during prosecution of EP2115147, dated Jun. 5, 2012, 1 page.
Reply to communication from the Examining Division, filed during prosecution of EP2115147, dated Aug. 20, 2010, 4 pages.
Reply to communication from the Examining Division, filed during prosecution of EP2115147, dated May 26, 2011, 3 pages.
Reply to communication from the Examining Division, filed during prosecution of EP2455473, dated Jul. 4, 2013, 4 pages.
Reply to communication from the Examining Division, filed during prosecution of EP2455473, dated Oct. 21, 2013, 1 page.
Reply to communication from the Examining Division, filed during prosecution of EP2455474, dated Jul. 4, 2013, 4 pages.
Reply to communication from the Examining Division, filed during prosecution of EP2455474, dated Dec. 8, 2015, 7 pages.
Reply to communication from the Examining Division, filed during prosecution of EP2455474, dated Mar. 17, 2017, 2 pages.
Reply to communication from the Examining Division, filed during prosecution of EP2455475, dated Jul. 5, 2013, 4 pages.
Reply to communication from the Examining Division, filed during prosecution of EP2455475, dated Dec. 8, 2015, 7 pages.
Reply to communication from the Examining Division, filed during prosecution of EP2455476, dated Dec. 3, 2015, 7 pages.
Reply to communication from the Examining Division, filed during prosecution of EP2455476, dated Jul. 5, 2013, 4 pages.
Reply to communication from the Examining Division, filed during prosecution of EP2455477, dated Jul. 5, 2013, 4 pages.
Reply to communication from the Examining Division, filed during prosecution of EP2455477, dated Oct. 21, 2013, 1 page.
Reply to communication from the Examining Division, filed during prosecution of EP2455478, dated Jul. 5, 2013, 4 pages.
Reply to communication from the Examining Division, filed during prosecution of EP2455478, dated Dec. 11, 2015, 7 pages.
Reply to communication from the Examining Division, filed during prosecution of EP2455479, dated Jul. 5, 2013, 4 pages.
Reply to communication from the Examining Division, filed during prosecution of EP2455479, dated Dec. 8, 2015, 7 pages.
Reply to communication from the Examining Division, filed during prosecution of EP2455480, dated Dec. 3, 2015, 7 pages.
Reply to communication from the Examining Division, filed during prosecution of EP2455480, dated Jul. 8, 2013, 5 pages.
Reply to communication from the Examining Division, filed during prosecution of EP2455481, dated Dec. 3, 2015, 7 pages.
Reply to communication from the Examining Division, filed during prosecution of EP2455482, dated Jul. 8, 2013, 5 pages.
Reply to communication from the Examining Division, filed during prosecution of EP2455483, dated Jul. 8, 2013, 5 pages.
Reply to communication from the Examining Division, filed during prosecution of EP3024929, dated Oct. 15, 2018, 2 pages.
Reply to communication from the Examining Division, filed during prosecution of EP3094722, dated Jan. 17, 2018, 2 pages.
Reply to communication from the Examining Division, filed during prosecution of EP3094722, dated May 28, 2018, 1 page.

(56) References Cited

OTHER PUBLICATIONS

Reply to communication from the Examining Division, filed during prosecution of EP3167051, dated Apr. 17, 2018, 2 pages.
Reply to communication from the Examining Division, filed during prosecution of EP3167051, dated May 28, 2018, 1 page.
Reply to the invitation to remedy deficiencies, filed during prosecution of EP2115147, dated Jan. 27, 2010, 2 pages.
Reply to Written Opinion prepared by the EPO, filed during prosecution of EP2455473, dated Nov. 14, 2012, 3 pages.
Reply to Written Opinion prepared by the EPO, filed during prosecution of EP2455474, dated Nov. 14, 2012, 3 pages.
Reply to Written Opinion prepared by the EPO, filed during prosecution of EP2455475, dated Nov. 14, 2012, 3 pages.
Reply to Written Opinion prepared by the EPO, filed during prosecution of EP2455476, dated Nov. 14, 2012, 3 pages.
Reply to Written Opinion prepared by the EPO, filed during prosecution of EP2455477, dated Nov. 19, 2012, 3 pages.
Reply to Written Opinion prepared by the EPO, filed during prosecution of EP2455478, dated Nov. 19, 2012, 3 pages.
Reply to Written Opinion prepared by the EPO, filed during prosecution of EP2455480, dated Nov. 19, 2012, 3 pages.
Reply to Written Opinion prepared by the EPO, filed during prosecution of EP2455481, dated Nov. 19, 2012, 3 pages.
Request for further processing, filed during prosecution of EP3024929, dated Dec. 21, 2017, 2 pages.
Request for interpreters during oral proceedings, dated Sep. 14, 2017, filed during Opposition against EP2455473, 1 page.
Response to Non-Final Office Action, filed for U.S. Appl. No. 15/191,919, dated Aug. 22, 2018, 8 pages.
Response to Non-Final Office Action, filed for U.S. Appl. No. 15/314,778, dated Nov. 21, 2018, 8 pages.
Response to Restriction Requirement, filed for U.S. Appl. No. 15/314,778, dated Apr. 5, 2018, 8 pages.
Rijk Zwaan General Information Website, dated Jul. 11, 2014, filed in Opposition proceedings against EP2115147, Available Online at <http://www.rijkzwaan.com/wps/wcm/connect/RZ+Corporate/Rijk+Zwaan/Company/About+us/General+Information>, 1 page.
Rothrock et al., (2006). "Identification of Pythium-Resistant Cold-Tolerant Rice Germplasm through Controlled Environmental and Field Evaluations," Proceedings of the Thirty-First Rice Technical Working Group, Retrieved from the Internet http://www.uaex.edu/rtwg/Proceedings/2006/RTWG%20Proc%202006.pdf, [retrieved on Apr. 24, 2012], pp. 108-109.
Schlegel (2003). Encyclopedic dictionary of plant breeding and related subjects, Haworth Press Inc., Binghamton, New York, p. 235-236.
Sequence alignment of *Spinacia oleracea* DMR6 gene (Seq ID 80) and DMR6 protein (Seq ID 81) from EP2455473 with an alternative *Spinacia oleracea* DMR6 gene and DMR6 protein as identified in *Spinacia oleracea* L. accession SPI 173 {IPK, Gatersleben, Germany) and a number of spinach varieties, filed Aug. 25, 2016, in Opposition against EP2455473, 2 pages.
Smart et al., "Best Control of Downy Mildew in Cole Crops", Dept. of Plant Pathology and Plant-Microbe Biology, Cornell University, Geneva NY, filed Dec. 8, 2017, in Opposition against EP2455477, 2 pages.
Somssich et al., (2003). "Closing another gap in the plant SAR puzzle," Cell, 113(7):815-816.
Statement of grounds of appeal by Bird&Bird, filed in relation to EP2455473, dated Apr. 26, 2018, 10 pages.
Summary of the legal entity "Rijk Zwaan Zaadteelt en Zaadhandel B.V." obtained from the Dutch Chamber of Commerce, filed Jul. 11, 2014, in Opposition against EP2115147, 4 pages.
Summons to attend Oral Proceedings for case EP2455475, dated Mar. 22, 2016, in order to discuss outstanding objections under Articles 56 and 83 EPC, 7 pages.
Summons to attend Oral Proceedings pursuant to Rule 115(1) EPC, filed in Opposition against EP2455474, dated Jul. 13, 2016, 1 page.
Summons to attend Oral Proceedings pursuant to Rule 115(1) EPC, filed in Opposition against EP2455479, dated May 31, 2016, 5 pages.
Table 1: Spinach DMR6 mutants presented in O18, filed in Opposition against EP2455473, dated Oct. 20, 2017, 1 page.
Table on insufficiency of disclosure issues, filed Jul. 30, 2018, in Opposition against EP2455474, 3 pages.
Table on insufficiency of disclosure issues, filed Oct. 1, 2018, in Opposition against EP2455475, 3 pages.
Table on insufficiency of disclosure issues, filed Jul. 18, 2018, in Opposition against EP2455479, 3 pages.
Table with all insufficiency of disclosure issues, filed Apr. 26, 2018, in Appeal against EP2455473, 3 pages.
Third Party Observations, filed in Opposition aginast EP 2455474, dated Sep. 2, 2017 for EP Application No. 12155887, 2 pages.
Thomas et al., (1992). "Resistance to Race 2 of Peronospora parasitica in U.S. Plant Introductions of *Brassica oleracea* var. *capitata*," HortScience, 27(10):1120-1122.
TWV/40/11, "Report of the Technical Working Party for Vegetables," Jun. 16, 2006, UPOV, 40th session, Mexico, 57 pages.
Unpublished U.S. Appl. No. 16/252,463, filed Jan. 18, 2019, titled "Disease Resistant *Brassica* Plants," (Copy Not Attached).
Van Schie et al., Unpublished U.S. Appl. No. 16/055,697, filed Aug. 6, 2018, titled "Phytophthora Resistant Plants Belonging to the Solanaceae Family," (Copy Not Attached).
Vicente et al. (2013). "*Xanthomonas campestris* pv. campestris (cause of black rot of crucifers) in the genomic era is still a worldwide threat to *Brassica* crops," Molecular Plant Pathology, 14(1): 2-18.
Vogel et al., (2013). "Insights into the regulation of protein abundance from proteomic and transcriptomic analyses," Nat. Rev. Genet., 13(4):227-232.
Vogel, et al. (2002). "PMR6, a Pectate Lyase-Like Gene Required for Powdery Mildew Susceptibility in *Arabidopsis*", The Plant Cell, vol. 14, pp. 2095-2106.
Wikipedia, "Expressed sequence tag", website as of Dec. 11, 2018, available online at <https://en.wikipedia.org/wiki/Expressed_sequence_tag>, filed during opposition of EP2455479, 4 pages.
Wikipedia, "Gene silencing", website as of Jul. 10, 2018, available online at <https://en.wikipedia.org/wiki/Gene_silencing>, filed during opposition of EP2455479, 12 pages.
Wikipedia, "Hyaloperonospora Brassicae", website as of Sep. 20, 2017, available online at <https://en.wikipedia.org/wiki/Hyaloperonospora_brassicae>, filed during opposition of EP2455477, 2 pages.
Wikipedia, "Hyaloperonospora Parasitica", website as of Sep. 20, 2017, available online at <https://en.wikipedia.org/wiki/Hyaloperonospora_parasitica>, filed during opposition of EP2455477, 3 pages.
Wilmouth et al., (2002). "Structure and Mechanism of Anthocyanidin Synthase from *Arabidopsis thaliana*," Structure, 10(1):93-103.
Withdrawal of a request for oral proceedings, filed during prosecution of EP2455482, dated Jan. 8, 2016, 1 page.
Withdrawal of a request for oral proceedings, filed during prosecution of EP2455483, dated Jan. 8, 2016, 1 page.
Withdrawal of an appeal, filed during appeal of EP2455477, dated Sep. 20, 2018, 1 page.
Written submission in preparation to/during oral proceedings, filed during prosecution of EP2455474, dated Oct. 10, 2016, 2 pages.
Written submission in preparation to/during oral proceedings, filed during prosecution of EP2455475, dated Aug. 30, 2016, 3 pages.
Written submission in preparation to/during oral proceedings, filed during prosecution of EP2455476, dated Jul. 21, 2016, 4 pages.
Written submission in preparation to/during oral proceedings, filed during prosecution of EP2455478, dated Oct. 10, 2016, 2 pages.
Written submission in preparation to/during oral proceedings, filed during prosecution of EP2455479, dated Oct. 5, 2016, 4 pages.
Written submission in preparation to/during oral proceedings, filed during prosecution of EP2455480, dated Jul. 21, 2016, 4 pages.
Written submission in preparation to/during oral proceedings, filed during prosecution of EP2455481, dated Aug. 30, 2016, 3 pages.
Written submission in preparation to/during oral proceedings, filed during prosecution of EP2455482, dated Oct. 13, 2015, 8 pages.

(56) References Cited

OTHER PUBLICATIONS

Written submission in preparation to/during oral proceedings, filed during prosecution of EP2455483, dated Oct. 13, 2015, 8 pages.
Zhang et al. (2017). "S5H/DMR6 Encodes a Salicylic Acid 5-Hydroxylase that Fine-Tunes Salicylic Acid Homeostasis," Plant Physiology Preview, DOI:10.1104/pp.17.00695, 41 pages.
Alignment of cucumber DMR6-specific primers with XP_008462902.2, filed on May 5, 2019 in Opposition proceedings against EP2455475, 1 page.
Applicant request for correction/amendment of the text proposed for grant with amended claims and description, filed Feb. 5, 2019 in case EP3094722, 22 pages.
Blast query of the sequence of Fig. 4 against Spinacia oleracea, filed in Opposition against EP2455473, dated Sep. 4, 2018, 6 pages.
Brewer et al., (2014). "Mutations in the *Arabidopsis* homoserine kinase gene DMR1 confer enhanced resistance to Fusarium culmorum and F. graminearum11," BMC Plant Biology, 14(1):317.
Communication from the Opposition Division in case EP2455474 dated Jun. 27, 2019, concerning the staying of opposition proceedings, 2 pages.
Communication from the Opposition Division in case EP2455475 dated Jun. 27, 2019, concerning the staying of opposition proceedings, 2 pages.
Communication from the Opposition Division in case EP2455479 dated Jun. 28, 2019, concerning the staying of opposition proceedings, 4 pages.
Communication from the Examining Division in case EP3024929 dated Jul. 9, 2019, concerning the staying of examination proceedings, 3 pages.
Communication from the Examining Division in case EP3094722 dated Jun. 27, 2019, concerning the staying of examination proceedings, 3 pages.
Communication from the Examining Division in case EP3167051 dated Jun. 27, 2019, concerning the staying of examination proceedings, 3 pages.
Database UniProt, (Nov. 22, 2017). "Putative Homoserine Kinase," XP002780503, Retrieved from Database Accession No. A0A251 RZ18, 1 page.
Decision T 1063/18, filed on Apr. 29, 2019 in Opposition proceedings against EP2455475, 29 pages.
Ferreyra et al., (2015). "The Identification of Maize and *Arabidopsis* Type I Flavone Synthases Links Flavones with Hormones and Biotic Interactions," Plant Physiology, 169:1090-1107.
MRNA sequence ID XM_008464687.2 corresponding to melon DMR6 protein sequence ID XP_008462909.2, filed on Apr. 29, 2019 in Opposition proceedings against EP2455475, 2 pages.
Preliminary Amendment, filed for U.S. Appl. No. 16/450,881, dated Jun. 25, 2019, 6 pages.
Reply of the patent proprietor to the notice(s) of opposition dated Apr. 29, 2019, filed in Opposition against EP2455475, 38 pages.
Response to Final Office Action, filed for U.S. Appl. No. 15/191,919, dated Apr. 25, 2019, 9 pages.
Response to Final Office Action, filed for U.S. Appl. No. 15/314,778, dated Aug. 26, 2019, 10 pages.
Response to Non-Final Office Action, filed for U.S. Appl. No. 15/594,293, dated Feb. 28, 2019, 11 pages.
Response to Notice to File Missing Parts and Notice of Omitted Items in a Nonprovisional Application, and Preliminary Amendment, filed for U.S. Appl. No. 16/361,089, dated Jul. 2, 2019, 37 pages.
Solanum tuberosum naringenin, 2-oxoglutarate 3-dioxygenase-like (LOC102590513), mRNA, Dec. 12, 2013, cited in Chinese Application No. 2014800731630 Office Action dated Feb. 19, 2019, 2 pages.
Solanum tuberosum naringenin, 2-oxoglutarate 3-dioxygenase-like (LOC102604390), mRNA, Dec. 12, 2013, cited in Chinese Application No. 2014800731630 Office Action dated Feb. 19, 2019, 2 pages.
Unpublished U.S. Appl. No. 16/659,470, filed Oct. 21, 2019, titled "Disease Resistant Potato Plants," (Copy not submitted here with pursuant to the waiver of 37 C.F.R. § 1.98(a)(2)(iii)).

\* cited by examiner

DOWNY MILDEW RESISTANCE PROVIDING GENES IN SUNFLOWER

CROSS-REFERENCE TO RELATED APPLICATIONS

This application is a Continuation application of U.S. patent application Ser. No. 14/906,666, internationally filed Jul. 21, 2014, which is a U.S. National Phase application under 35 U.S.C. § 371 of International Application No. PCT/EP2014/065641, filed Jul. 21, 2014, which claims priority to International Application No. PCT/EP2013/065397, filed Jul. 22, 2013, each of which is incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 701802011801SEQLIST.TXT, date recorded: May 21, 2018, size: 10 KB).

The present invention relates to downy mildew resistant genes in sunflower and especially to downy mildew resistance sunflower plants. The present invention further relates to methods for obtaining the present downy mildew resistant sunflower plants and the use of the present genes for providing downy mildew resistance in sunflower.

*Helianthus* L. is a genus of plants comprising about 52 species in the *Asteraceae* family. The common designation "sunflower" is generally used to indicate the annual species *Helianthus annuus*. *Helianthus annuus* and other species such as Jerusalem artichoke (*Helianthus tuberosus*), are cultivated in temperate regions as food crops and ornamental plants. The domesticated sunflower, *Helianthus annuus*, is the most familiar species of the *Helianthus* L. genus. *Helianthus annuus* is cultivated both for ornamental purposes as for providing vegetable oil from seeds.

Downy mildew, a common and destructive disease in sunflowers, is capable of killing or stunting plants, reducing stand and causing significant yield loss (up to 50 to 95%). Sunflowers are most susceptible to downy mildew in fields where heavy rain has fallen within 2-3 weeks after planting.

Downy mildew refers to any of several types of oomycete plant pathogens that are obligate parasites of plants. Downy mildews exclusively belong to *Peronosporaceae*. The downy mildew pathogen generally causing downy mildew disease in cultivated sunflowers is designated *Plasmopara halstedii* or *Plasmopara helianthi*.

In the technical field of sunflower cultivation and breeding, there is a constant need to identify new resistance genes against downy mildew. However, most resistance gene identified are monogenic dominant resistance genes and the resistance provided by these genes is generally rapidly broken because downy mildew pathogens evolve and adapt at a high frequency thereby regaining the ability to successfully infect a host plant. Accordingly, there is a continuous need in dc art for new resistance genes, preferably resistance genes of which the resistance is not readily broken by adaptation of the pathogen.

A disadvantage of known sunflower resistance genes is that, besides providing pathogen resistance, these genes often are accompanied by undesired phenotypes such as stunted growth or spontaneous occurrence cell death. Accordingly, there is a continuous need in the art for new resistance genes not providing, besides the resistance, undesirable phenotypes.

It is an object of the present invention, amongst other objects, to meet, at least partially if not fully, the above needs of the art.

This object of the present invention, amongst other objects, is met by providing a sunflower plants and resistance genes as outlined in the appended claims.

Specifically, this object of the present invention, amongst other objects, is met, according to a first aspect, by sunflower plants being resistant to the plant pathogen downy mildew, wherein the present plant comprises a downy mildew resistance conferring gene encoding (a) protein(s) comprising the amino acid sequence as shown in SEQ ID No. 2 and/or SEQ ID NO. 4 or a downy mildew resistance conferring gene encoding a protein with more than 90% sequence identity, preferably more than 94% sequence identity, more preferably more than 96% sequence identity with identity SEQ ID No. 2 and/or SEQ ID NO. 4 and wherein the expression of the present resistance conferring gene is reduced as compared to the expression of the present resistance conferring gene in a sunflower plant not being resistant to the plant pathogen downy mildew or the enzymatic activity of the present protein is reduced as compared to the enzymatic activity of the present protein in a sunflower plant not being resistant to the plant pathogen downy mildew.

In the research that led to the present invention, it was surprisingly found that a reduced expression of the present genes or a reduced enzymatic activity of the present proteins provided a broad and durable resistance to downy mildew in sunflower plants.

According to the present invention, an expression is reduced in comparison with the expression of the present resistance conferring gene in a sunflower plant not being resistant to the plant pathogen downy mildew. The term "not being resistant" indicates a resistance level, determined in an appropriate disease test and using an appropriate reference plant such as a parent plant, being less than the resistance level observed in the present plants. Accordingly, the present resistance can also be designated as an increased resistance to downy mildew. Suitable reference plants according to the invention, besides parent plants, can also be plants generally designated in the art as downy mildew susceptible plants.

A suitable disease test is inoculating plants with a downy mildew pathogen and subsequently observing the occurrence of disease symptoms such as large, angular or blocky, yellow areas visible on the upper surface of leaves or destroyed leaf tissue.

Expression levels in the present plants and the reference plants can be determined using any suitable and generally known Molecular Biology technique such as a quantitative Polymerase Chain Reaction (PCR) or mRNA hybridization.

According to the present invention, an enzymatic activity is reduced in comparison with the activity of the present protein in a sunflower plant not being resistant to the plant pathogen downy mildew. The term "not being resistant" indicates a resistance level, determined in an appropriate disease test and using an appropriate reference plant, such as a parent plant, being less than the resistance level observed in the present plants. Accordingly, the present resistance can also be designated as an increased resistance to downy mildew. Suitable reference plants according to the invention can, besides parent plants, also be plants generally designated in the art as downy mildew susceptible plants. A suitable disease test is inoculating plants with downy mildew and subsequently observing the occurrence of disease symptoms such as large, angular or blocky, yellow areas visible on the upper surface of leaves or destroyed leaf tissue.

The present proteins have a 2-oxoglutarate FE(II)-dependent oxygenase activity. The enzyme has an absolute requirement for Fe(II) and catalyzes two-electron oxidations, including hydroxylation, desaturation and oxidative ring closure reactions. The oxidation of the 'prime' substrate is coupled to the conversion of 2OG into succinate and $CO_2$. One of the oxygens of the dioxygen molecule is incorporated into succinate. In the case of desaturation reactions, the other dioxygen-derived oxygen is presumably converted to water. In hydroxylation reactions, the partial incorporation of oxygen from dioxygen into the alcohol product occurs with significant levels of exchange of oxygen from water being observed. Accordingly, the present reduced activity can be determined using an assay measuring compounds being either the starting compounds or the resulting compounds of the enzymatic reaction. As a suitable alternative, protein levels, being inherently indicative of a reduced activity, of the present proteins can be determined by, for example, ELISA or protein hybridization both being techniques commonly known to the skilled person.

Within the context of the present invention, resistance to downy mildew is individually or in combination provided, through reduced expression or activity, to the present sunflower plants by the present proteins or genes encoding the present proteins.

The present sunflower plants can be obtained by mutagenesis of downy mildew susceptible plant or downy mildew resistant plants thereby increasing the resistance thereof. For example, mutations, either at the expression level or the protein level, can be introduced in these plants by using mutagenic chemicals such as ethyl methane sul2fonate (EMS) or by irradiation of plant material with gamma rays or fast neutrons. The resulting mutations can be directed or random. In the latter case, mutagenized plants carrying mutations in the present resistance conferring genes can be readily identified by using the TILLING (Targeting Induced Local Lesions IN Genomes) method (McCallum et al. (2000) Targeted screening for induced mutations. Nat. Biotechnol. 18, 455-457, and Henikoff et al. (2004) TILLING. Traditional mutagenesis meets functional genomics. Plant Physiol. 135, 630-636). Briefly, this method is based on the PCR amplification of a gene of interest from genomic DNA of a large collection of mutagenized plants in the M2 generation. By DNA sequencing or by scanning for point mutations using a single-strand specific nuclease, such as the CEL-I nuclease (Till et al. (2004) Mismatch cleavage by single-strand specific nucleases. Nucleic Acids Res. 32, 2632-2641) individual plants having a mutation in the present genes are identified.

According to a preferred embodiment of this first aspect of the present invention, the present downy mildew pathogens are *Plasmopara halstedii* and/or *Plasmopara helianthi*. However, other pathogens belonging to the *Peronosporaceae* and capable of causing downy mildew disease in sunflower are contemplated within the context of the present invention.

According to another preferred embodiment of this first aspect of the present invention, the present reduced enzymatic activity is provided by one or more mutations in the coding sequence of the present genes resulting in a truncated or non-functional protein. Truncated proteins can be readily determined by analyzing gene transcripts at the mRNA or cDNA level and non-functional proteins can be determined in enzyme assays or using conformation-dependent antibodies. Mutations which can be assayed at the transcript level are, for example, amino acid substitutions, frame-shifts or pre-mature stop codons.

According to an especially preferred embodiment of this first aspect of the present invention, the present mutations resulting in a reduced activity of the present proteins are mutations resulting in the absence of or amino acid substitution(s) in the sequence motif "WRDYLR" or Trp-Arg-Asp-Tyr-Leu-Arg of the coding sequence of the present resistance providing gene. The present sequence motif can be found at amino acid positions 123 to 128 of SEQ ID NO:2 and at amino acid positions 132 to 137 of SEQ ID NO:4. The present inventors have found that mutations in this region especially affect the downy mildew resistance phenotype, i.e. level of resistance, observed. Especially mutations involving Y (Tyr) and/or R (Arg) are highly correlated with the downy mildew resistance phenotype, i.e. level of resistance, observed.

According to yet another preferred embodiment this first aspect of the present invention, the present reduced expression is provided by one or more mutations in the regulatory regions or non-coding sequences of the present genes. Examples of regulatory regions of the present genes are promotor and terminator regions and examples of non-coding regions are introns and especially splicing influencing motifs therein.

According to a second aspect, the present invention provides seeds, plant tissues or plants parts of the sunflower plants as described above or obtainable from the sunflower plants as described above, comprising a downy mildew resistance conferring gene encoding a protein comprising the amino acid sequence as shown in SEQ ID No. 2 and/or SEQ ID NO. 4 or a downy mildew resistance conferring gene encoding a protein with more than 90% sequence identity, preferably more than 94% sequence identity, more preferably more than 96% sequence identity with identity SEQ ID No. 2 and/or SEQ ID NO. 4 and the expression of the resistance conferring gene is reduced as compared to the expression of the resistance conferring gene in a sunflower plant not being resistant to the plant pathogen downy mildew or the enzymatic activity of the protein is reduced as compared to the enzymatic activity of the protein in a sunflower plant not being resistant to the plant pathogen downy mildew.

According to a third aspect, the present invention relates to methods for providing sunflower plants being resistant, or methods for increasing the resistance of sunflower plants, to the plant pathogen downy mildew wherein the present methods comprise the step of introducing in a sunflower plant a downy mildew resistance conferring gene encoding a protein comprising the amino acid sequence as shown in SEQ ID No. 2 and/or SEQ ID NO. 4 or a downy mildew resistance conferring gene encoding a protein with more than 90% sequence identity, preferably more than 94% sequence identity, more preferably more than 96% sequence identity with identity SEQ ID No. 2 and/or SEQ ID NO. 4 and the expression of the resistance conferring gene is reduced as compared to the expression of the resistance conferring gene in the starting sunflower plant or the enzymatic activity of the protein is reduced as compared to the enzymatic activity of the protein in the starting sunflower plant not being resistant to the plant pathogen downy mildew.

According to a fourth aspect, the present invention relates to the use of a gene, or the cDNA sequence thereof, encoding a protein comprising the amino acid sequence as shown in SEQ ID No. 2 or SEQ ID NO. 4 or a downy mildew resistance conferring gene encoding a protein with more than 90% sequence identity, preferably more than 94% sequence identity, more preferably more than 96% sequence identity with identity SEQ ID No. 2 or SEQ ID NO. 4 for providing sunflower plants being resistant or having an increased resistance to the plant pathogen downy mildew.

According to a fifth aspect, the present invention relates to proteins having an amino acid sequence comprising SEQ ID No. 2 or SEQ ID No. 4.

According to a sixth aspect, the present invention relates to nucleic acid sequences comprising SEQ ID No. 1 or SEQ ID NO. 3.

According to a seventh aspect, the present invention relates to gene encoding a protein having an amino acid sequence comprising SEQ ID No. 2 or SEQ ID No. 4 or a nucleic acid sequence comprising SEQ ID No. 1 or SEQ ID NO. 3.

```
HaTZ-1 ortholog protein
MAGKVISSGIQYTTLPDSYVRPVNDRPNLSQVSECNDVPVIDIGGADREL
ISRQIGDACRHYGFFQVINHGVADELVKKMEQVGRDFFQLPVEEKMKLYS
EDPIKTMRLSTSFNVKKEQVHNWRDYLRLHCYPLDQYSPEWPSNPCYFKE
YVGNYCIAVRELGMRILEFISESLGLEKERLNMILGEQGQHMAINHYPVC
PEPELTYGLPGHTDPNALTILLQDTLVSGLQVQKDGKWVAVKPHPNAFVI
NIGDQLEALSNGEYKSVWHRAVVNSDQPRMSIASFLCPCNDSVLSAPNEL
IKDGSTRVFKDFTYTEYYKKFWSRNLDQEHCLEFFKN*

HaTZ-1 ortholog CDS:
ATGGCGGGAAAAGTCATCTCCAGTGGCATCCAATACACTACTTTACCCGA
CAGTTACGTCCGTCCGGTCAACGACAGGCCTAACCTATCCCAAGTCTCCG
AATGCAACGATGTTCCGGTTATCGACATCGGTGGAGCTGACCGGGAGCTC
ATAAGCCGGCAAATCGGCGATGCGTGCCGTCACTACGGCTTTTTCCAGGT
GATAAACCACGGTGTGGCGGATGAATTGGTGAAGAAGATGGAGCAGGTAG
GGAGAGATTTCTTCCAGTTGCCGGTTGAGGAGAAGATGAAGCTCTACTCG
GAGGATCCGACGAAGACGATGAGGCTTTCGACGAGCTTCAACGTCAAGAA
AGAACAAGTGCATAACTGGAGGGATTATCTCCGGCTTCACTGCTATCCTT
TGGATCAGTACTCTCCTGAATGGCCTTCCAATCCTTGTTATTTCAAAGAA
TATGTTGGAAATTACTGTATAGCGGTACGCGAATTAGGGATGAGGATACT
TGAATTCATATCGGAAAGTTTAGGTTTAGAAAAAGAGCGACTAAATATGA
TATTAGGCGAGCAAGGACAACATATGGCCATCAACCATTATCCAGTGTGC
CCTGAACCTGAGTTAACTTATGGGTTGCCTGGTCACACTGATCCTAATGC
ACTCACCATACTCCTTCAAGACACGCTTGTCTCTGGATTACAAGTTCAAA
AAGATGGCAAATGGGTAGCGGTTAAACCACACCCTAACGCGTTTGTCATC
AACATTGGCGACCAACTAGAGGCGTTGAGTAATGGTAATACAAGAGTGT
GTGGCATCGAGCCGTGGTCAACTCAGACCAACCAAGAATGTCAATAGCTT
CGTTTTTGTGTCCCTGTAATGACTCAGTCCTCAGCGCTCCTAACGAACTA
ATAAAAGATGGATCGACGCGTGTTTTCAAAGACTTTACTTACACAGAATA
CTACAAGAAGTTTTGGAGTCGAAATCTAGACCAAGAACATTGTTTAGAGT
TCTTCAAGAACTAG HaTZ-2 ortholog protein
MATTSKRLLVSDLVSTDKIDQVPSNYIRPITQRPNFQNVVRDSIPLIDLK
DLNGPNHANVIKQIGQACADHGFFQVKNHGVPESIIANMMQTARDFFNLP
EQERLKNYSDDPTKTTRLSTSFNIRTEKVANWRDYLRLHCYPIDNFIDEW
PTNPASFRAHVAEYCQSTRNLALQLIAAISESLGLHKDYMNTQLGKHAQH
MVLNYYPPCPQPDLTYGLPGHTDPNFITILLQDEVPGLQVLKDGKWVAVD
PVPNTFIINIGDQVQVMSNDKYKSILHRAVVNCDKERISIPTFYCPSPEA
VIGPAPEVVTDDEPAVYRQFTYGEYYEKFWDNGLEKCLDMFKTS*

HaTZ-2 ortholog CDS:
ATGGCTACCACCTCAAAAAGATTACTAGTTAGCGACCTCGTATCCACCGA
TAAAATCGACCAAGTCCCTTCAAACTACATCCGACCCATCACCCAACGTC
CCAATTTCCAAAATGTTGTTCGCGACTCCATCCCTCTCATTGACCTCAAA
GATCTCAACGGCCCCAATCACGCTAACGTGATCAAACAAATCGGTCAAGC
TTGCGCTGATCACGGCTTCTTCCAGGTTAAAAACCATGGCGTACCCGAAT
CCATCATAGCCAACATGATGCAAACCGCTCGAGACTTCTTCAACCTACCC
GAACAAGAACGACTCAAAAACTATTCAGATGACCCCACAAAGACCACTAG
ACTCTCCACCAGCTTCAACATACGAACCGAAAAGGTCGCAAACTGGAGAG
ATTACTTACGACTCCATTGCTACCCGATCGATAACTTCATCGACGAATGG
CCAACCAATCCGGCCTCGTTTCGGGCCCATGTAGCGGAGTATTGCCAGAG
TACAAGAAACTTAGCACTCCAACTTATTGCAGCCATTTCAGAAAGCTTAG
GACTTCATAAAGACTACATGAACACACAGTTAGGGAAGCATGCTCAGCAT
ATGGTCTTGAACTACTACCCACCATGCCCACAACCCGATTTAACATACGG
GTTACCCGGACACACTGATCCTAATTTCATCACCATCCTTCTTCAAGATG
AGGTTCCTGGTCTTCAGGTCTTGAAAGATGGTAAATGGGTAGCGGTTGAT
CCGGTTCCAAACACTTTCATCATCAACATTGGTGATCAAGTTCAGGTGAT
GAGTAATGATAAGTACAAGAGTATTTTGCATCGAGCTGTGGTGAATTGTG
ATAAAGAACGGATATCTATACCGACTTTCTACTGTCCGTCGCCTGAGGCG
GTTATCGGGCCTGCTCCCGAGGTTGTAACTGATGATGAGCCTGCTGTGTA
TCGACAGTTTACTTATGGGGAGTACTATGAGAAGTTTTGGGACAATGGGC
TTGAGAAGTGTTTGGATATGTTCAAGACTAGTTGA
```

The invention claimed is:

1. An isolated sunflower plant resistant to *Plasmopara halstedii* or *Plasmopara helianthi*, wherein the sunflower plant has a reduced level or reduced activity of a protein comprising the amino acid sequence of SEQ ID NO:2 or SEQ ID NO:4 as compared to a sunflower plant that is not resistant to *Plasmopara halstedii* or *Plasmopara helianthi*, wherein said reduced level or reduced activity is the result of a mutation in the coding sequence of a gene encoding the protein of SEQ ID NO:2 or SEQ ID NO:4, wherein the mutation results in a truncated or non-functional protein of SEQ ID NO:2 or SEQ ID NO:4, and wherein said mutation in the coding sequence of said gene results in one or more amino acid substitutions in the sequence motif "WRDYLR" (SEQ ID NO:5).

2. The sunflower plant according to claim 1, wherein the sunflower plant has said reduced level or reduced activity of a protein comprising the amino acid sequence of SEQ ID NO:2.

3. The sunflower plant according to claim 1, wherein the sunflower plant has said reduced level or reduced activity of a protein comprising the amino acid sequence of SEQ ID NO:4.

4. A seed, tissue, or plant part of the sunflower plant according to claim 1, wherein the seed, tissue, or plant part comprises the mutation in the gene encoding the protein of SEQ ID NO:2 or SEQ ID NO:4 and has a reduced level or reduced activity of the protein of SEQ ID NO:2 or SEQ ID NO:4.

5. A seed, tissue, or plant part of the sunflower plant according to claim 2, wherein the seed, tissue, or plant part comprises the mutation in the gene encoding the protein of SEQ ID NO:2 and has a reduced level or reduced activity of the protein of SEQ ID NO:2.

6. A seed, tissue, or plant part of the sunflower plant according to claim 3, wherein the seed, tissue, or plant part comprises the mutation in the gene encoding the protein of SEQ ID NO:4 and has a reduced level or reduced activity of the protein of SEQ ID NO:4.

7. A method for obtaining a sunflower plant which is resistant to *Plasmopara halstedii* or *Plasmopara helianthi* comprising reducing an endogenous level or an endogenous activity of a protein comprising the amino acid sequence of SEQ ID NO:2 or SEQ ID NO:4 in a sunflower plant as compared to a sunflower plant that is not resistant to *Plasmopara halstedii* or *Plasmopara helianthi* by introducing a non-natural mutation into a coding sequence of a gene encoding the protein of SEQ ID NO:2 or SEQ ID NO:4, wherein the mutation results in a truncated or non-functional protein of SEQ ID NO:2 or SEQ ID NO:4, and wherein said mutation in the coding sequence of said gene results in one or more amino acid substitutions in the sequence motif "WRDYLR" (SEQ ID NO:5).

8. A sunflower plant produced from the method according to claim 7, wherein the plant comprises the mutation in the gene encoding the protein of SEQ ID NO:2 or SEQ ID NO:4 and has a reduced level or reduced activity of the protein of SEQ ID NO:2 or SEQ ID NO:4.

9. A seed, tissue, or plant part of the sunflower plant according to claim 8, wherein the seed, tissue, or plant part comprises the mutation in the gene encoding the protein of SEQ ID NO:2 or SEQ ID NO:4 and has a reduced level or reduced activity of the protein of SEQ ID NO:2 or SEQ ID NO:4.

10. A method for obtaining a sunflower plant which is resistant to *Plasmopara halstedii* or *Plasmopara helianthi* comprising reducing an endogenous level or an endogenous activity of a protein comprising the amino acid sequence of SEQ ID NO:2 in a sunflower plant as compared to a sunflower plant that is not resistant to *Plasmopara halstedii* or *Plasmopara helianthi* by introducing a non-natural mutation into a coding sequence of a gene encoding the protein of SEQ ID NO:2, wherein the mutation results in a truncated or non-functional protein of SEQ ID NO:2, and wherein said mutation in the coding sequence of said gene results in one or more amino acid substitutions in the sequence motif "WRDYLR" (SEQ ID NO:5).

11. A sunflower plant produced from the method of claim 10, wherein the plant comprises the mutation in the gene encoding the protein of SEQ ID NO:2 and has a reduced level or reduced activity of the protein of SEQ ID NO:2.

12. A seed, tissue, or plant part of the sunflower plant according to claim 11, wherein the seed, tissue, or plant part comprises the mutation in the gene encoding the protein of SEQ ID NO:2 and has a reduced level or reduced activity of the protein of SEQ ID NO:2.

13. A method for obtaining a sunflower plant which is resistant to *Plasmopara halstedii* or *Plasmopara helianthi* comprising reducing an endogenous level or an endogenous activity of a protein comprising the amino acid sequence of SEQ ID NO:4 in a sunflower plant as compared to a sunflower plant that is not resistant to *Plasmopara halstedii* or *Plasmopara helianthi* by introducing a non-natural mutation into a coding sequence of a gene encoding the protein of SEQ ID NO:4, wherein the mutation results in a truncated or non-functional protein of SEQ ID NO:4, and wherein said mutation in the coding sequence of said gene results in one or more amino acid substitutions in the sequence motif "WRDYLR" (SEQ ID NO:5).

14. A sunflower plant produced from the method of claim 13, wherein the plant comprises the mutation in the gene encoding the protein of SEQ ID NO:4 and has a reduced level or reduced activity of the protein of SEQ ID NO:4.

15. A seed, tissue, or plant part of the sunflower plant according to claim 14, wherein the seed, tissue, or plant part comprises the mutation in the gene encoding the protein of SEQ ID NO:4 and has a reduced level or reduced activity of the protein of SEQ ID NO:4.

* * * * *

SEQUENCE LISTING

<160> NUMBER OF SEQ ID NOS: 5

<210> SEQ ID NO 1
<211> LENGTH: 1014
<212> TYPE: DNA
<213> ORGANISM: Helianthus annuus

<400> SEQUENCE: 1

```
atggcgggaa aagtcatctc cagtggcatc caatacacta ctttacccga cagttacgtc      60
cgtccggtca acgacaggcc taacctatcc caagtctccg aatgcaacga tgttccggtt     120
atcgacatcg gtggagctga ccgggagctc ataagccggc aaatcggcga tgcgtgccgt     180
cactacggct ttttccaggt gataaaccac ggtgtggcgg atgaattggt gaagaagatg     240
gagcaggtag ggagagattt cttccagttg ccggttgagg agaagatgaa gctctactcg     300
gaggatccga cgaagacgat gaggctttcg acgagcttca acgtcaagaa agaacaagtg     360
cataactgga gggattatct ccggcttcac tgctatcctt tggatcagta ctctcctgaa     420
tggccttcca atccttgtta tttcaaagaa tatgttggaa attactgtat agcggtacgc     480
gaattaggga tgaggatact tgaattcata tcggaaagtt taggtttaga aaaagagcga     540
ctaaatatga tattaggcga gcaaggacaa catatggcca tcaaccatta tccagtgtgc     600
cctgaacctg agttaactta tgggttgcct ggtcacactg atcctaatgc actcaccata     660
ctccttcaag acacgcttgt ctctggatta caagttcaaa aagatggcaa atgggtagcg     720
gttaaaccac accctaacgc gtttgtcatc aacattggcg accaactaga ggcgttgagt     780
aatggtgaat acaagagtgt gtggcatcga gccgtggtca actcagacca accaagaatg     840
tcaatagctt cgttttgtg tccctgtaat gactcagtcc tcagcgctcc taacgaacta     900
ataaagatg gatcgacgcg tgttttcaaa gactttactt acacagaata ctacaagaag     960
ttttggagtc gaaatctaga ccaagaacat tgtttagagt tcttcaagaa ctag          1014
```

<210> SEQ ID NO 2
<211> LENGTH: 337
<212> TYPE: PRT
<213> ORGANISM: Helianthus annuus

<400> SEQUENCE: 2

```
Met Ala Gly Lys Val Ile Ser Ser Gly Ile Gln Tyr Thr Thr Leu Pro
1               5                   10                  15

Asp Ser Tyr Val Arg Pro Val Asn Asp Arg Pro Asn Leu Ser Gln Val
            20                  25                  30

Ser Glu Cys Asn Asp Val Pro Val Ile Asp Ile Gly Gly Ala Asp Arg
        35                  40                  45

Glu Leu Ile Ser Arg Gln Ile Gly Asp Ala Cys Arg His Tyr Gly Phe
    50                  55                  60

Phe Gln Val Ile Asn His Gly Val Ala Asp Glu Leu Val Lys Lys Met
65                  70                  75                  80

Glu Gln Val Gly Arg Asp Phe Phe Gln Leu Pro Val Glu Glu Lys Met
                85                  90                  95

Lys Leu Tyr Ser Glu Asp Pro Thr Lys Thr Met Arg Leu Ser Thr Ser
            100                 105                 110

Phe Asn Val Lys Lys Glu Gln Val His Asn Trp Arg Asp Tyr Leu Arg
        115                 120                 125

Leu His Cys Tyr Pro Leu Asp Gln Tyr Ser Pro Glu Trp Pro Ser Asn
    130                 135                 140

Pro Cys Tyr Phe Lys Glu Tyr Val Gly Asn Tyr Cys Ile Ala Val Arg
145                 150                 155                 160

Glu Leu Gly Met Arg Ile Leu Glu Phe Ile Ser Glu Ser Leu Gly Leu
                165                 170                 175

Glu Lys Glu Arg Leu Asn Met Ile Leu Gly Glu Gln Gly Gln His Met
            180                 185                 190
```

```
Ala Ile Asn His Tyr Pro Val Cys Pro Glu Pro Glu Leu Thr Tyr Gly
            195                 200                 205

Leu Pro Gly His Thr Asp Pro Asn Ala Leu Thr Ile Leu Leu Gln Asp
    210                 215                 220

Thr Leu Val Ser Gly Leu Gln Val Gln Lys Asp Gly Lys Trp Val Ala
225                 230                 235                 240

Val Lys Pro His Pro Asn Ala Phe Val Ile Asn Ile Gly Asp Gln Leu
                245                 250                 255

Glu Ala Leu Ser Asn Gly Glu Tyr Lys Ser Val Trp His Arg Ala Val
            260                 265                 270

Val Asn Ser Asp Gln Pro Arg Met Ser Ile Ala Ser Phe Leu Cys Pro
    275                 280                 285

Cys Asn Asp Ser Val Leu Ser Ala Pro Asn Glu Leu Ile Lys Asp Gly
    290                 295                 300

Ser Thr Arg Val Phe Lys Asp Phe Thr Tyr Thr Glu Tyr Tyr Lys Lys
305                 310                 315                 320

Phe Trp Ser Arg Asn Leu Asp Gln Glu His Cys Leu Glu Phe Phe Lys
                325                 330                 335

Asn
```

<210> SEQ ID NO 3
<211> LENGTH: 1035
<212> TYPE: DNA
<213> ORGANISM: Helianthus annuus

<400> SEQUENCE: 3

```
atggctacca cctcaaaaag attactagtt agcgacctcg tatccaccga taaaatcgac      60
caagtccctt caaactacat ccgacccatc acccaacgtc ccaatttcca aaatgttgtt     120
cgcgactcca tccctctcat tgacctcaaa gatctcaacg ccccaatca cgctaacgtg     180
atcaaacaaa tcggtcaagc ttgcgctgat cacggcttct tccaggttaa aaaccatggc     240
gtacccgaat ccatcatagc caacatgatg caaaccgctc gagacttctt caacctaccc     300
gaacaagaac gactcaaaaa ctattcagat gaccccacaa agaccactag actctccacc     360
agcttcaaca tacgaaccga aaaggtcgca aactggagag attacttacg actccattgc     420
tacccgatcg ataacttcat cgacgaatgg ccaaccaatc cggcctcgtt tcgggcccat     480
gtagcggagt attgccagag tacaagaaac ttagcactcc aacttattgc agccatttca     540
gaaagcttag acttcataa agactacatg aacacacagt tagggaagca tgctcagcat     600
atggtcttga actactaccc accatgccca caacccgatt taacatacgg gttacccgga     660
cacactgatc ctaatttcat caccatcctt cttcaagatg aggttcctgg tcttcaggtc     720
ttgaaagatg gtaaatgggt agcggttgat ccggttccaa acactttcat catcaacatt     780
ggtgatcaag ttcaggtgat gagtaatgat aagtacaaga gtattttgca tcgagctgtg     840
gtgaattgtg ataaagaacg gatatctata ccgactttct actgtccgtc gcctgaggcg     900
gttatcgggc ctgctcccga ggttgtaact gatgatgagc tgctgtgta tcgacagttt     960
acttatgggg agtactatga gaagttttgg gacaatgggc ttgagaagtg tttggatatg    1020
ttcaagacta gttga                                                    1035
```

<210> SEQ ID NO 4
<211> LENGTH: 344
<212> TYPE: PRT
<213> ORGANISM: Helianthus annuus

```
<400> SEQUENCE: 4

Met Ala Thr Thr Ser Lys Arg Leu Leu Val Ser Asp Leu Val Ser Thr
1               5                   10                  15

Asp Lys Ile Asp Gln Val Pro Ser Asn Tyr Ile Arg Pro Ile Thr Gln
            20                  25                  30

Arg Pro Asn Phe Gln Asn Val Arg Asp Ser Ile Pro Leu Ile Asp
        35                  40                  45

Leu Lys Asp Leu Asn Gly Pro Asn His Ala Asn Val Ile Lys Gln Ile
    50                  55                  60

Gly Gln Ala Cys Ala Asp His Gly Phe Phe Gln Val Lys Asn His Gly
65              70                  75                  80

Val Pro Glu Ser Ile Ile Ala Asn Met Met Gln Thr Ala Arg Asp Phe
                85                  90                  95

Phe Asn Leu Pro Glu Gln Glu Arg Leu Lys Asn Tyr Ser Asp Asp Pro
            100                 105                 110

Thr Lys Thr Thr Arg Leu Ser Thr Ser Phe Asn Ile Arg Thr Glu Lys
        115                 120                 125

Val Ala Asn Trp Arg Asp Tyr Leu Arg Leu His Cys Tyr Pro Ile Asp
    130                 135                 140

Asn Phe Ile Asp Glu Trp Pro Thr Asn Pro Ala Ser Phe Arg Ala His
145                 150                 155                 160

Val Ala Glu Tyr Cys Gln Ser Thr Arg Asn Leu Ala Leu Gln Leu Ile
                165                 170                 175

Ala Ala Ile Ser Glu Ser Leu Gly Leu His Lys Asp Tyr Met Asn Thr
            180                 185                 190

Gln Leu Gly Lys His Ala Gln His Met Val Leu Asn Tyr Tyr Pro Pro
        195                 200                 205

Cys Pro Gln Pro Asp Leu Thr Tyr Gly Leu Pro Gly His Thr Asp Pro
    210                 215                 220

Asn Phe Ile Thr Ile Leu Leu Gln Asp Glu Val Pro Gly Leu Gln Val
225                 230                 235                 240

Leu Lys Asp Gly Lys Trp Val Ala Val Asp Pro Val Pro Asn Thr Phe
                245                 250                 255

Ile Ile Asn Ile Gly Asp Gln Val Gln Val Met Ser Asn Asp Lys Tyr
            260                 265                 270

Lys Ser Ile Leu His Arg Ala Val Val Asn Cys Asp Lys Glu Arg Ile
        275                 280                 285

Ser Ile Pro Thr Phe Tyr Cys Pro Ser Pro Glu Ala Val Ile Gly Pro
    290                 295                 300

Ala Pro Glu Val Val Thr Asp Asp Glu Pro Ala Val Tyr Arg Gln Phe
305                 310                 315                 320

Thr Tyr Gly Glu Tyr Tyr Glu Lys Phe Trp Asp Asn Gly Leu Glu Lys
                325                 330                 335

Cys Leu Asp Met Phe Lys Thr Ser
            340

<210> SEQ ID NO 5
<211> LENGTH: 6
<212> TYPE: PRT
<213> ORGANISM: Helianthus annuus

<400> SEQUENCE: 5

Trp Arg Asp Tyr Leu Arg
1               5
```